United States Patent [19]
Rodriguez et al.

[11] Patent Number: 5,707,636
[45] Date of Patent: Jan. 13, 1998

[54] APPARATUS AND METHOD FOR PREPARING SOLID FORMS WITH CONTROLLED RELEASE OF THE ACTIVE INGREDIENT

[75] Inventors: Lorenzo Rodriguez, Zola Predosa; Maurizio Cini, Bologna; Cristina Cavallari, Bologna; Giuseppe Motta, Bologna, all of Italy

[73] Assignee: Saitec S.R.L., Bologna, Italy

[21] Appl. No.: 624,475

[22] PCT Filed: Apr. 6, 1995

[86] PCT No.: PCT/IT95/00048

§ 371 Date: Jun. 20, 1996

§ 102(e) Date: Jun. 20, 1996

[87] PCT Pub. No.: WO96/03979

PCT Pub. Date: Feb. 15, 1996

[30] Foreign Application Priority Data

Aug. 3, 1994 [IT] Italy .................. BO94A0379

[51] Int. Cl.$^6$ .................. A61K 9/14; A61K 3/02; A01N 25/00; B05C 19/02
[52] U.S. Cl. .................. 424/401; 424/405; 424/408; 424/409; 424/489; 424/497; 118/57; 118/300; 118/612; 118/639; 118/654; 204/157.15; 204/157.62; 427/2.15; 427/475; 427/478; 427/480
[58] Field of Search .................. 424/401, 490, 424/405, 408, 409, 489, 497; 204/157.15, 157.62; 118/57, 300, 612, 639, 654, DIG. 5; 427/475, 478, 480, 2.15

[56] References Cited

U.S. PATENT DOCUMENTS

| | | |
|---|---|---|
| 2,828,206 | 3/1958 | Rosenberg . |
| 3,078,216 | 2/1963 | Greif . |
| 3,432,593 | 3/1969 | Shepard . |
| 3,922,339 | 11/1975 | Shear . |
| 4,341,759 | 7/1982 | Bogentoft et al. . |
| 4,572,833 | 2/1986 | Pedersen et al. . |
| 4,657,543 | 4/1987 | Langer et al. . |
| 4,779,806 | 10/1988 | Langer et al. . |
| 4,877,620 | 10/1989 | Loew et al. .................. 424/468 |

FOREIGN PATENT DOCUMENTS

| | | |
|---|---|---|
| 0 438 359 | 7/1991 | European Pat. Off. . |
| 0 467 743 | 1/1992 | European Pat. Off. . |
| 2 571 980 | 4/1986 | France . |
| 27 25 849 | 12/1978 | Germany . |
| 1044572 | 10/1966 | United Kingdom . |
| 90/13780 | 11/1990 | WIPO . |

OTHER PUBLICATIONS

John et al., "Surfactant Effects on Spray–Congealed Formulations of Sulfaethylthiadiazol–Wax", Journal of Pharmaceutical Sciences, vol. 57, No. 4, Apr. 1968, pp. 584–589.

Patent Abstract of Japan JP 9091084, See abstract.

Patent Abstract of Japan JP 60094403, See abstract.

Patent Abstract of Japan JP 47020327, See abstract.

Primary Examiner—Thurman K. Page
Assistant Examiner—M. Sikha
Attorney, Agent, or Firm—Cushman Darby & Cushman Intellectual Property Group of Pillsbury Madison & Sutro LLP

[57] ABSTRACT

Controlled release solid forms, apparatus and method for preparing solid forms for controlled release of an active ingredient.

10 Claims, 15 Drawing Sheets

APPARATUS AND METHOD FOR PREPARING SOLID FORMS WITH CONTROLLED RELEASE OF THE ACTIVE INGREDIENT

This application is a 35USC 371 application of PCT/IT95/00048, filed Apr. 6, 1995.

TECHNICAL FIELD

The present invention relates to an apparatus and a method for preparing solid forms with controlled release of the active ingredient. More particularly, it relates to an apparatus for preparing solid forms with controlled release of the active ingredient utilizing the well known spray drying and spray congealing techniques, and a method for preparing said solid forms employing said apparatus. The solid forms thus obtained can be used in the pharmaceutical field for the oral administration in the form of powders with controlled release, or as intermediates for obtaining further forms such as capsules, tablets, suspensions and the like, or they can be used in cosmetic, fragrances, preservants, alimentary as well as in veterinary field or, when for releasing vegetal hormones, pesticides, or fertilizers, also in agroindustrial field.

BACKGROUND ART

The controlled release of an active ingredient from a solid form containing it, is well known in the art. Generally, said systems contain a) one or more excipients which modulate the release acting as disgregating agents or as solubilizers, wetting agents etc., and/or b) one or more polymeric or lipidic materials acting as barriers limiting the release and capable to control the release rate of the therapeutic agent. Said excipients should be logically compatible with the active ingredients and the administration site, stable in the action site, capable to interact with the active ingredient and the biologic fluids so as to provide the desired release control. They should be also easy available and not expensive. It is thus evident that the search for excipients always more sophisticated and adaptable to the different requirements is not presently ended.

Thus in U.S. Pat. No. 2,828,206 discrete, free flowing particles are described, each comprising at least one inner core of fat-soluble vitamin material, said core being coated with a shell of a fat-insoluble substance selected from the group consisting of protein, gums, carbohydrates and pectin, which is in turn coated with a member of the group consisting of fats and waxes having a melting point between 45° and 95° C.

GB-A-1,044,572 claims a pharmaceutical composition providing prolonged release of a drug in the gastro-intestinal tract comprising a multitude of medicinal pallets randomly coated with a fatty acid coating comprising a saturated fatty acid or mixture of saturated fatty acids having from 12 to 22 carbon atoms per molecule, said coating being modified by an inert dusting powder which serves to form channels or pores through the otherwise continuous coating.

In U.S. Pat. No. 4,341,759 granules containing a pharmaceutically active material and at least one pharmaceutically inactive release controlling component are described, wherein said granules have a core and an outer layer comprising at least one active compound and at least one inactive release controlling substance over a period of time sufficient to cause said unitary layer to form on each core to give granules of size 0.3–2 mm.

U.S. Pat. No. 4,572,833 relates to a method for preparing a pharmaceutical oral controlled release composition, in which individual units comprise units of an active substance which is subject to controlled release as a result of coating the units with a substantially water- insoluble but water-diffusable controlled release coating comprising applying, on units comprising the active substance, a film-coating mixture comprising a solvent, a film-forming substance dissolved in the solvent and a hydrophobic substance substantially micro- dispersed in the film-coating mixture in a molten, but undissolved state, the film-coating mixture being applied at a temperature above the melting point of the hydrophobic substance.

U.S. Pat. No. 3,078,216 describes an oral pharmaceutical prepara- tion having a prolonged release comprising a plurality of medicament granules, substantially all being from 12 mesh to 80 mesh, each coated with a layer of water insoluble, partly digestible hydrophobic material, the thickness of coating varying directly with particle size whereby in oral use the very fine granules rapidly release their medicament and the granules of increasing size release their medicament more and more slowly.

In U.S. Pat. No. 3,922,339 a process of preparing a sustained release pharmaceutical preparation of a medicament is described, which comprises (1) blending a medicament with desired inert materials, (2) wetting the blend with sufficient liquid material so as to act as a binder on compacting, (3) compacting the wetted blend by extruding to form a spaghetti-like material, (4) drying, breaking and screening the extruded material to the desired particle size, (5) spraying the particles with a solution of a film-forming material, (6) dusting the sprayed particles with a powder and drying to form a seal on the particles, and (7) coating the sealed particles with a solution of an excipient so as to form an enteric-soluble coating on the sealed particle.

From U.S. Pat. No. 3,432,593 a granule, capsule or tablet is known, having the active medicament adsorbed on a complex colloidal magnesium aluminum silicate. The individual granules may be further provided with one or more suitable retardant coatings, each of which provides a predetermined period of sustainment.

From what stated above, it is clear that the controlled release technique has been widely used and studied, but the attempts to effect new improvements thereon go on unceasingly. As a rule, it can be stated that several and different reasons exhist for coating or encapsulating an active ingredient with a particular matrix. That is: a) protection from environmental agents, b) conversion fron liquid into solid, c) reduction of gastric irritation, d) masking of taste and smell, e) separation of incompatible substances, f) controlled release, g) reduction and removal of dust and electrostatic charges.

At present, the most utilized techniques for obtaining solid forms, in particular powders, are those utilizing the solidification of the matrix, that is the so called spray drying and spray congealing techniques.

The spray drying technique comprises essentially the following steps:

- solubilizing the active ingredient or disperding it as a core in a solution of an encapsulating material at a suitable temperature;
- spraying the mixture in the form of minute droplets (atomization) by means of a rotating atomizer or a nozzle in a drying chamber;
- introducing at the same time in the drying chamber, in addition to said mixture, a hot air stream that can be introduced in equicurrent or countercurrent with the mixture. However, it is necessary a good mixing of the droplets with the air stream.

As in the drying chamber the vaporization of the solvent (s) from the droplets is quick because of the great available evaporation surface, said vaporization allows to maintain the temperature of the droplets on a low level and to minimize the heating time;

collecting the dried product at the bottom of the drying chamber or forwarding it to a cyclone.

With this technique, often porous microspheres are obtained, suitable for example to mask the taste but not well suited for preparing controlled release drugs.

Spray congealing is very-similar to spray drying, but it differs from the former in that the coating material does not need a solvent for its use. Said coating material should be melted at a suitable temperature and, when sprayed in spray-dryer, it requires cold air instead of hot air for having the droplets solidified. In said technique, very important are the additives employed together with the material forming the matrix. They are able to speed up or to slow down the release of a drug or the intestinal adsorption, for example of a vitamin.

Either of the two techniques is employed, logically the large dimensions of the used equipment should be taken into consideration. In a experimental work to examine the effects of surface active agents on formulations of sulfaethylthiadiazole with waxes as coating material, a laboratory apparatus had for example a collection chamber approximately 274.3 cm (9 ft.) high (Journal of Pharmaceutical Sciences, vol. 57, no.4, April 1968, page 584–589). The diameter of this chamber must be almost half of its height, otherwise the walls are too much soiled by the melted material. A reduction of the chamber size is impossible, in that a considerable atomizing jet is always achieved.

It is thus evident that also said quite advanced techniques, as well as other ones for having controlled release compositions, for example compacting, extrusion, film-forming, etc., are not free from problems and disadvantages.

Attempts have been made to solve at last partly all these problems employing ultrasonic energy. Thus in EP-A-0 467 743 a process for compacting a powder mixture is described, in which a non-thermoplastic product is blended with a thermoplastic one and the mixture thus obtained is submitted to ultrasonic energy with pressure. An adsorbing tablet is thus formed that can be imbued with a perfume and applied on the skin, or an adsorbing strip which can be imbued with a drug.

In U.S. Pat. No. 4,657,543 a process for delivering a biologically active substance on demand is described, said process comprising the steps of combining a biologically active substance with a biocompatible polymeric composition as an admixture, forming said admixture into a shaped, solid polymeric matrix, implanting said solid polymeric matrix in vivo at a preselected site such that said solid implanted matrix is in a liquid environment, and exposing said implanted solid polymeric matrix to ultrasonic energy for a predetermined time to effect cavitation of said solid polymeric matrix by rapid compression with subsequent expansion of liquid or solid surrounding said solid polymeric matrix thereby to control the rate of release of said biologically active substance from said matrix over a specific time period wherein the rate of release is changed during said time period.

From U.S. Pat. No. 4,779,806 a process for delivering a composition on demand is at last known, which comprises incorporating said composition within a polymeric matrix, surrounding said composition and polymeric matrix with a liquid medium, and exposing said polymeric matrix to ultrasonic energy for a predetermined time and and at a frequency to effect cavitation of said polymeric matrix to release said composition from said matrix in a controlled manner over a specific time period.

In JP-9091084 the preparation of a controlled realease drug is described, which is obtained by emulsifying with ultrasounds an aqueous solution of the drug in an organic solvent containing the biocompatible polymeric material.

In JP-47020327 the welding with ultrasounds of a sandwich is described, comprising two equal or different polymer sheets surrounding the active ingredient.

In JP-60094403 mixtures of cyclodextrin and alpha-tocopherol are at last described, obtained by stirring intimately the mixture with the aid of ultrasounds.

In all the literature mentioned above, with controlled release of a drug almost always a delayed release is meant, that is a release that permits the drug to be released slowly to the body. In both the last mentioned US patents use was then made of ultrasonic energy for having cavitation of a polymeric matrix, but also in this case a delayed release is achieved and it is necessary to implant a matrix in vivo and to degrade the matrix for having the desired release. It is also known that cavitation exhibits a few disadvantages, the main of which is a loss of efficiency and risk for the health.

DISCLOSURE OF INVENTION

It was thus object of the present invention to overcome the disadvantages mentioned above and to provide an improved apparatus and method for obtaining solid forms with controlled release of the active ingredient utilizing the spray drying and spray congealing techniques. It was thus object of the present invention to minimize the overall dimensions of the equipment necessary to utilize said techniques, and also avoid the disadvantages associated with the solvent recovery and the danger of explosions. At the same time it was a further object of the present invention to provide solid forms from which the active ingredient could be released in a delayed or rapid but controlled manner based upon the choice of the excipients, and that could be employed with the most active ingredients actually used in compositions with controlled release in the pharmaceutical, cosmetic, alimentary and agricultural field.

This aim could be surprisingly attained by means of an apparatus working essentially according to the classic scheme of a spray drying or spray congealing procedure, but with the use of an ultrasonic atomizer instead of those normally employed, that is with compressed air, airless or centrifugal.

BRIEF DESCRIPTION OF THE DRAWING

FIGS. 1*a*–1*d* depicts the type of sonotrodes used in the invention.

FIG. 2 shows an ibuprofen release rate.

FIGS. 3, 4 and 6 show a ketoprofen release rate.

FIG. 5 shows a naproxen release rate.

FIGS. 7–23 represent photographs of miocrospheres.

The present invention provides accordingly an improved apparatus for preparing solid forms with controlled release of the active ingredient, comprising:

a) an atomizer nebulizing the liquid to be treated in minute droplets, said liquid being a solution, suspension or emulsion of one or more active ingredients and/or excipients solubilized in one or more solvents of different polarity in the case of spray drying, or solutions or suspensions of one or more active ingredients in one or more waxy melted excipients in the case of pray congealing;

b) a cylindrical chamber with vertical axis, in the inside of which the droplets obtained by means of a) fall and are transformed in spherical particles of powder owing to the evaporation of the solvents contained therein or to the quenching solidification of the waxy melted components, and c) a device suitable for the quantitative recovery of the volatile, eventually employed solvents.

The atomizer a) employs the vibration of metal resonant elements or of a suitable nozzle to give droplets having a diameter of from 5 to 500 μm according to the applied intensity and mechanical frequency, as well to the geometry of the mechanical device and the chemico-physical characteristics of the treated liquids, such as viscosity, surface tension, weight density, etc. With the term mechanical vibrations as use therein, in the above and following description always ultrasonic, sonic or infrasonic vibrations are meant.

As resonant metal elements, appropriately shaped or with vibrating elements sonotrodes can be used, for example thin plates, or with a nozzle. When a nozzle is employed, its diameter will depend logically on the liquid used to obtain the corresponding powder.

In FIG. 1 three types of sonotrodes are illustrated, and with thick line arrow the liquid feeding to be treated, whereas with thin line the small droplets so obtained, and in particular A) with an axially perforated nozzle, B) without nozzle with reflecting angled end, C) with planar vibrating plate. With D) another particular form of a vibrating, cuspidal plate is illustrated having a better reflection of the product to be treated.

The eployed thin plate can be made of steel or of another material able to be worked to give resistant, thin plates, not attackable by liquids or melts contacting them. Good results have been obtained with stainless steel plates. As material for the thin plates also titanium and Avional 2024 and 2018 (trade name for a aluminium alloy) can be used.

The chamber as indicated in b) can provide cold or hot air circulation, in equicurrent or countercurrent with the powder falling path so as to facilitate the drying or solidification process. Therefore, it can be provided with means able to remove the powder from air, for example cyclones, filters, etc.

As to the apparatus working of the present invention and the advantages attained, it is necessary to point out what follows.

The shape of the atomized fluid jet (particularly its length, usually 25–30 cm) allows to hold in a range of 1 meter maximum the diameter of the atomizing chamber without running into risk to stain the walls, and the height of said chamber can be lower than 2 meters because of the great thinnes with which the powder can be obtained, that slows down its fall, intensifying the drying rate. These two characteristics (diameter and height) can not be attained with the known equipments. Should a conventional nozzle be employed, at the same loading jets of a few meters can be observed and not of 25–30 cm as in the present invention.

Operating with a frequency of some kHz, the ultrasonic nozzle is able to dissipate relatively high energy and to atomize substantial amounts of liquid (50 l/h), thus obtaining large amounts of powder. O-wing to its own working, it is moreover self-cleaning so that no maintenance during the operation is necessary and it is possible to easily atomize also fluids like waxes, glycerides, melted polyethylene glycols that, because their unfavorable chemico-physical properties (in particular viscosity or surface tension), are difficult to atomize with conventional nozzles. In fact, it is known that surface tension of a drop with flat surface depends on material and temperature, whereas should the drop be convex, surface tension is in inverse relation to the drop bend radius. Very small droplets have therefore very high drying rates.

As the ultrasonic nozzle works without employing compressed air, it allows to work at reduced pressure, thus limitating or avoiding completely the introduction of air into the apparatus, and permitting a complete recovery of the volatile solvents eventually emoployed. They can be easily condensed by means of a simple compression at room temperature of their vapour with compressors without lubrication. The whole apparatus can moreover simply operate in absence of oxygen or outside the inflammability and explosiviness range of the employed solvents.

Further object of the present invention is also a method for preparing solid forms with controlled release of the active ingredient, said method being characterized in that a solution, suspension or emulsion of one or more active ingredients and/or excipients in one or more solvents of different polarity or of one or more active ingredients in one or more melted excipients is fed on vibrating metal elements or in a nozzle vibrating at infrasonic, sonic or ultrasonic frequency to give very small droplets of liquid that fall turning into spherical particles of powder owing to the evaporation of solvents or to quenching solidification of the melted waxy components, and the solvents are eventually recovered.

The frequency utilized for carrying out the present invention if of from 20 kHz to 150 kHz.

Illustrative examples of biologically active substances which can be atomized to give powders according to the method of the present invention are: vitamins, enzymes, antibiotics (such as tetracyclines, penicillins, cephalosporins), diuretics, sedatives, analgesics, bronchodilators, carotenoids, β-blockers, antinflammatories, antidepressives, antidiabetics, lipids, antihypertensives, vasodilators, vasoconstrictors, hormones, steroids, antihistamines, antitussives, alkaloids , amino acids, antipyretics, antibacterial agents, amphetamins, hypnotics, tranquilizers, symphatomimetics, barbiturics, antiparkinson agents, antimalarials, antispasmodics, several topic ophtalmic drugs and so on. Also interferon, antigens, antibodies, polysaccharides, growth factors, anticancer agents, phytohormones, pesticides, pheromones, fragrances, preservants, etc.

Typical examples of suitable drugs include: dexamethasone, prednisolone, isoproterenol, propranolol, codeine, atropine, hyoscyamine, streptomycin, cortisone, isosorbide-5-mononitrate, amobarbital, scopolamine, theophylline, ephedrine, urapidil, ketoprofen, paracetamol, indomethacin, diltiazem, diacerhein, phenylpropanolamine and biliary acids. Also interferon, antibodies, antigens, polysaccharides, growth factors, anti cancer drugs, phytohormones, pesticides, pheromones, fragrances, perfumes, etc.

The polymers or copolymers useful for preparing the matrix or for having a coating: which can be utilized alone or in any mixture thereof, comprise all those already employed in the controlled release pharmaceutical, cosmetic or agricultural compositions, for example cellulose and its derivatives, polyamides, acrylic polymers, polyesters, polyvinylpyrrolidone, starch, polyethylene glycols, polystyrene, polyvinylalcohol, myristyl alcohol and stearyl alcohol polymers, polyvinyl acetate, polybutadiene, polyvinyl formal, polyvinylbutyral, vinyl chloride-vinyl acetate copolymer, ethylene-vinyl acetate copolymer, vinyl chloride-propylene-vinyl acetate copolymer and any mixture thereof. The present invention is not restricted to the employed polymers or active ingredients.

Solvents that can be eventually used in the present invention comprise for example acetone, isopropyl alcohol, methylene chloride. Also plastifiers such as dibutyl phtalate and trimethyl citrate can be employed. Also aqueous solutions can be used.

The powders thus obtained can be perfectly gastroresistant but quickly soluble at neutral or basic pH in the case of pharmaceutical compositions (for example employing Eudragit S 100), or they are able to grant the release with kinetics very close to zero order and in a wide range of release constants (for example employing Eudragit RS, RL or mixture thereof or cellulose esters).

The powders thus obtained can be employed both directly as oral powders with controlled release, and as intermediates for producing further controlled release forms, such as tablets, capsules, suspensions and the like.

In order to evaluate the efficiency of the new apparatus and method object of the present invention, powders have been prepared from some active ingredients and their release as a function of time has been evaluated. The results are summarized in the enclosed drawings, in which.

The explanation of the other figures will be deduced from the following examples. The forms obtained with the apparatus of the present invention are also illustrated in the examples. As the examples are given for illustratiove purpose only, they have not to be considered as limitative of the present invention.

It is also clear that any person skilled in the art could modify the present invention utilizing another drug or different substances for having the powders. It appears thus to be superfluous to point out as said modifications belong in toto to the invention as described above, and therefore they could not be retained as different from the claims as reported here below.

EXAMPLE 1

Figure 4:
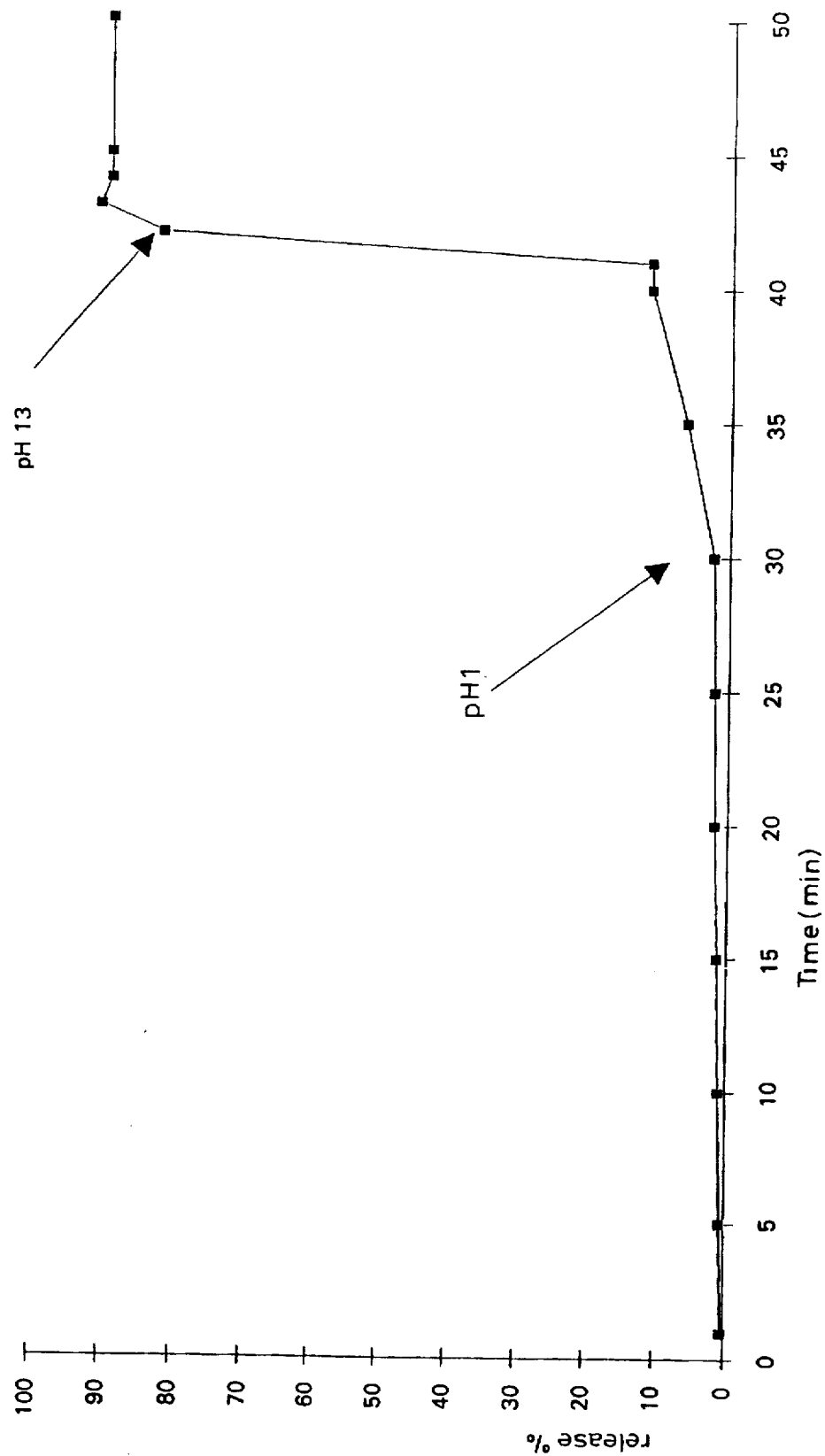
FIG. 4 shows ketoprofen release at the same conditions but in the presence of several excipients.

A solution was prepared comprising 1.5 g ketoprofen, 1.5 g Eudragit S 100 (Trade mark), 0.15 g Eudraflex (Trade mark) and 20 g of a 2:1 mixture of acetone and methylene chloride. This mixture was transferred at the rate of 50 l/h on an atomizer vibrating at 40 kHz. Very little droplets have been obtained that, owing to the solvents evaporation, falling in the air after a run of 1.5 m were trasnformed in perfectly spherical and essentially not porous particles. Evaluation of the active ingredient release by means of simulated gastric and enteric juice give the trend shown in FIG. 4.

EXAMPLE 2

Figure 5:
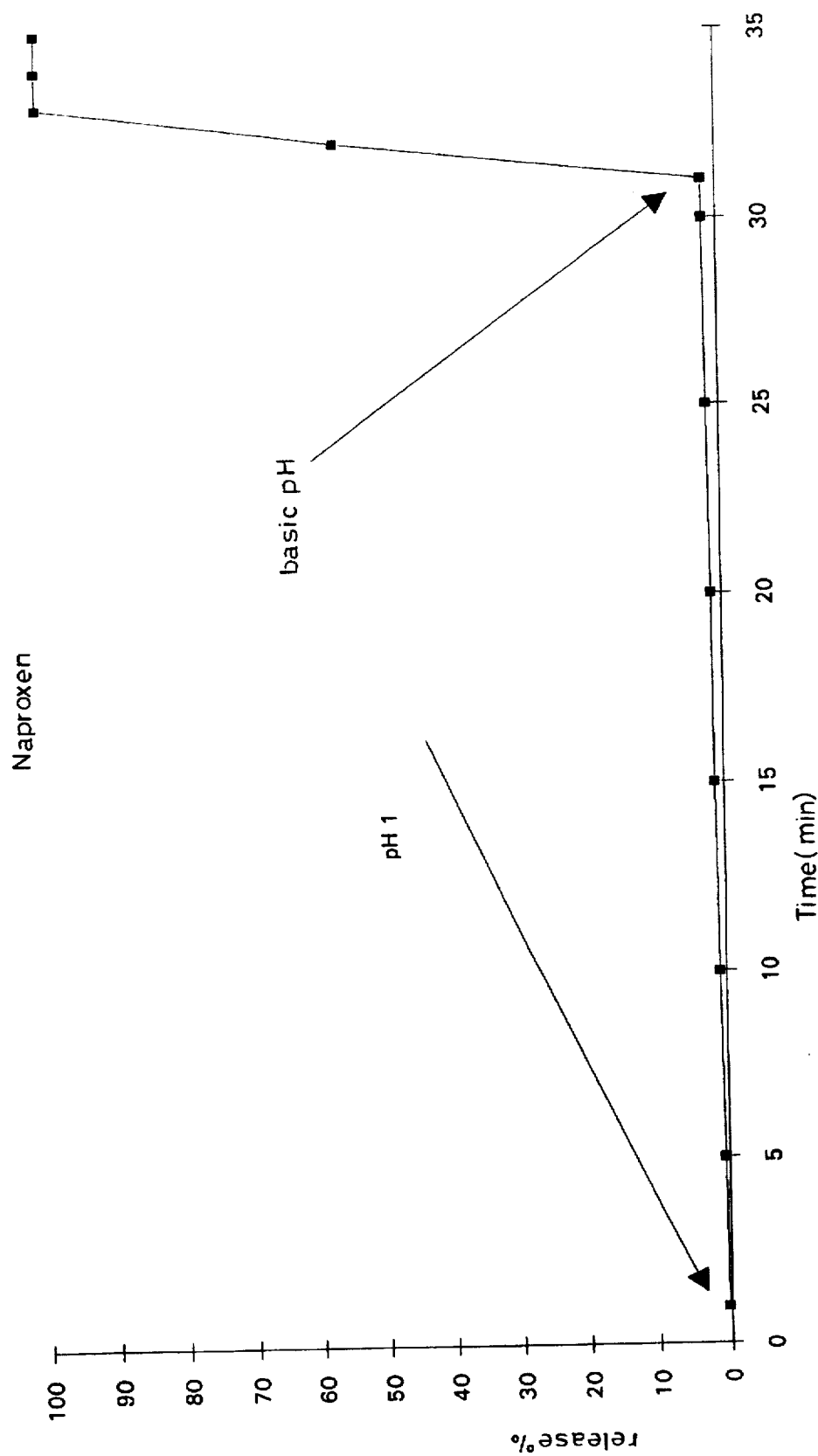
FIG. 5 shows the naproxen release at the same conditions.
Figure 6:
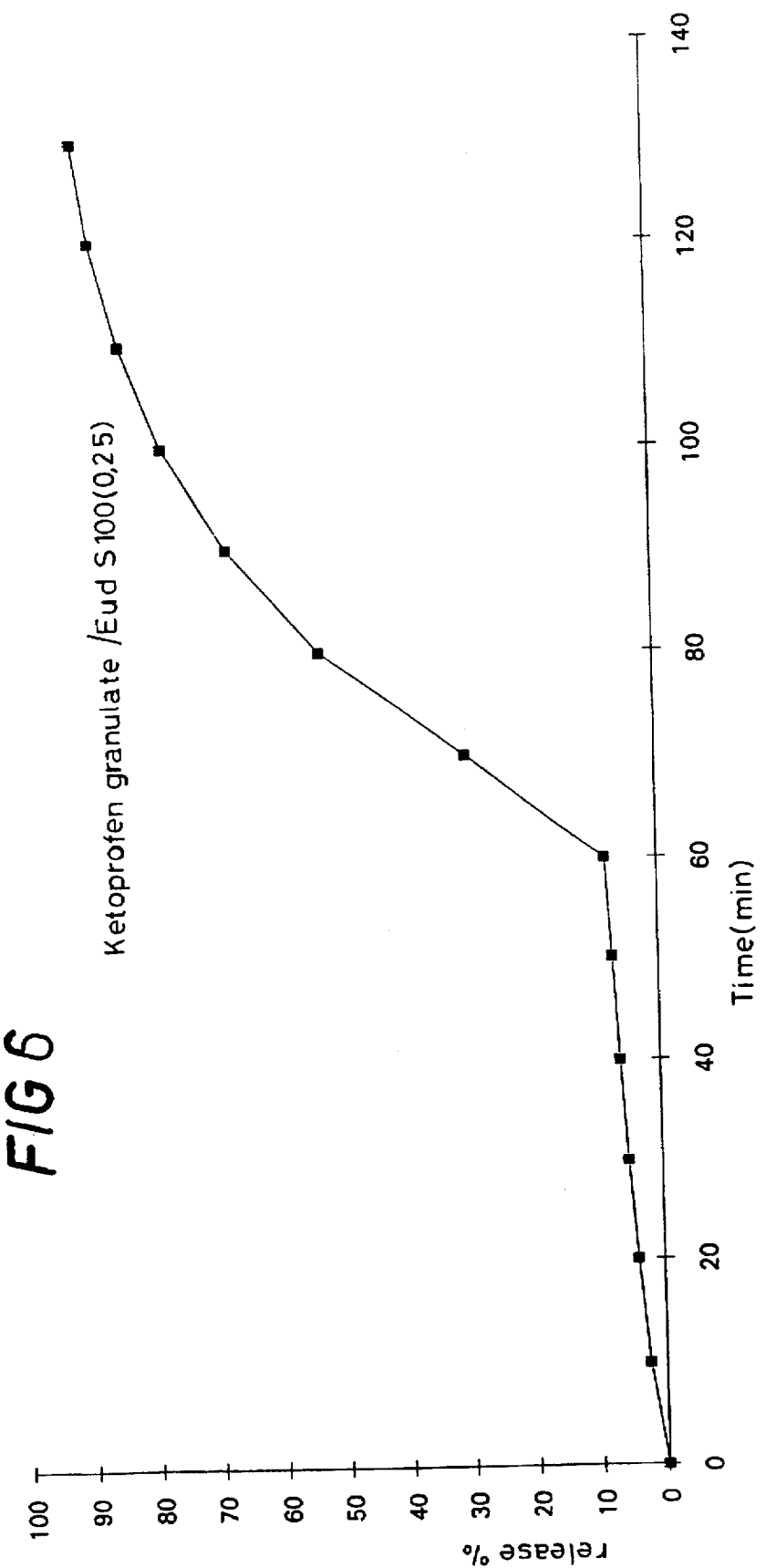
FIG. 6 shows for comparison purpose the release of an active ingredient from a pharmaceutical form obtained according to the co-pending application WO 94/14421, by compacting ketoprofen with talc, Eudragit S 100 and magnesium stearate with the aid of ultrasounds.

The procedure described in Example 1 was repeated, with the difference that 1.5 parts of naproxen were used instead of ketoprofen. The results of release tests in gastric and enteric simulated juice gave the curve trend shown in FIG. 5.

EXAMPLE 3

Figure 1A:
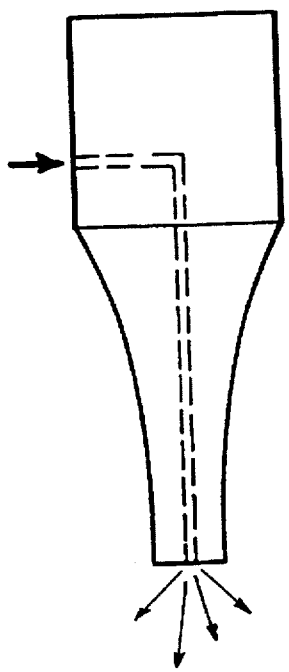
Figure 1B:
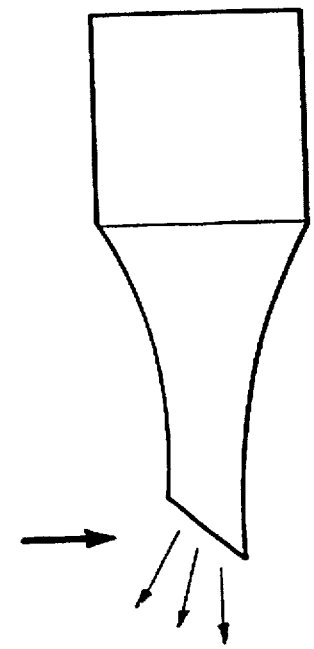
Figure 1C:
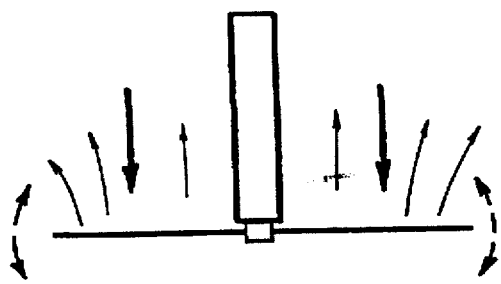
Figure 1D:
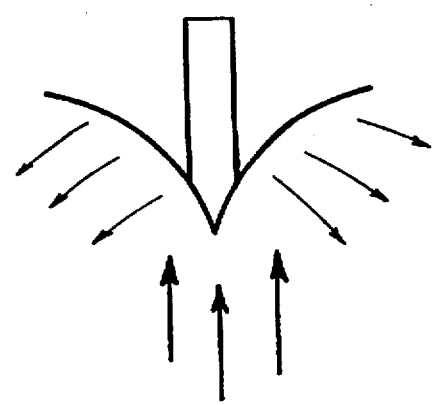
Figure 2:
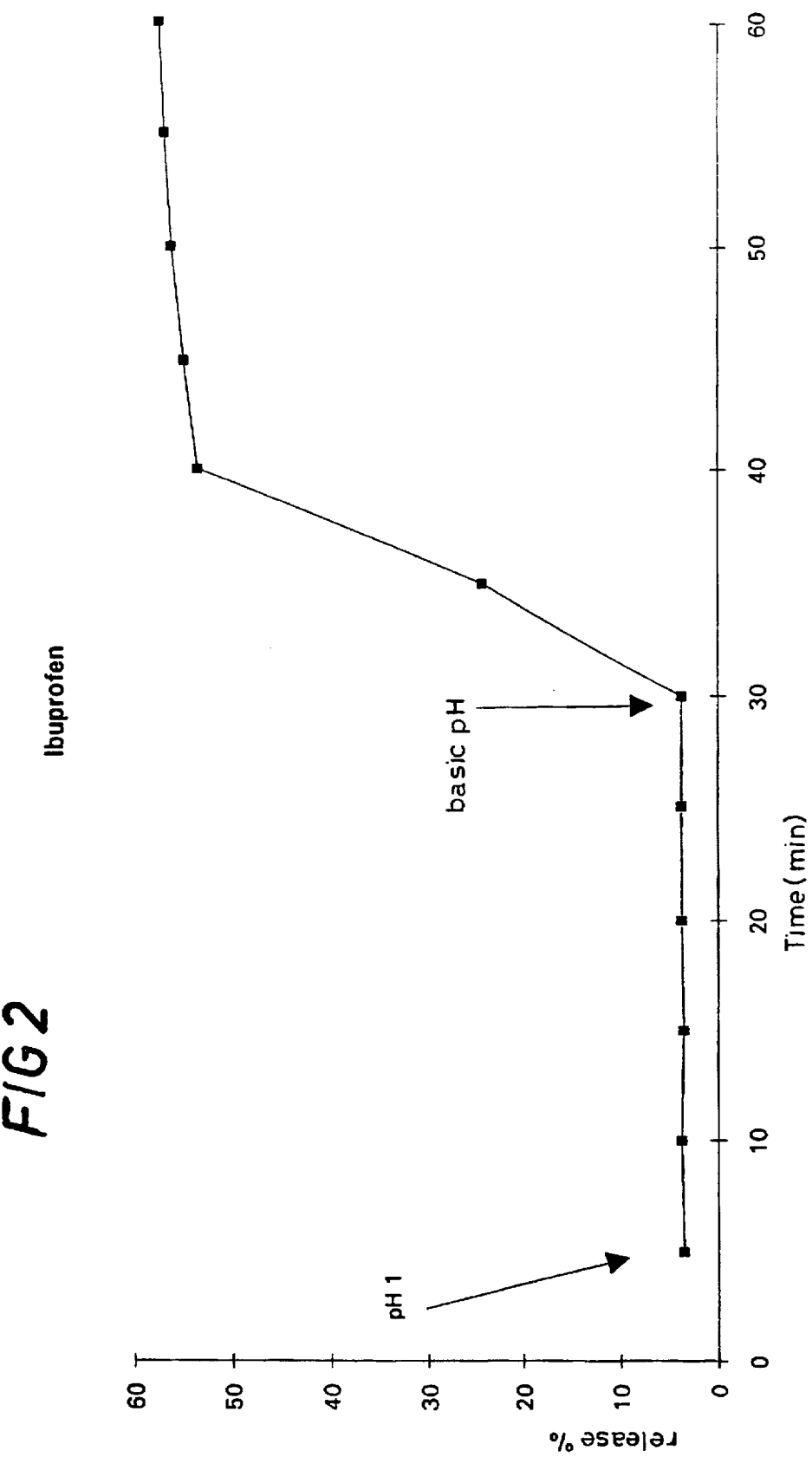
FIG. 2 shows ibuprofen release rate first in acid and then in basic medium.
Figure 3:
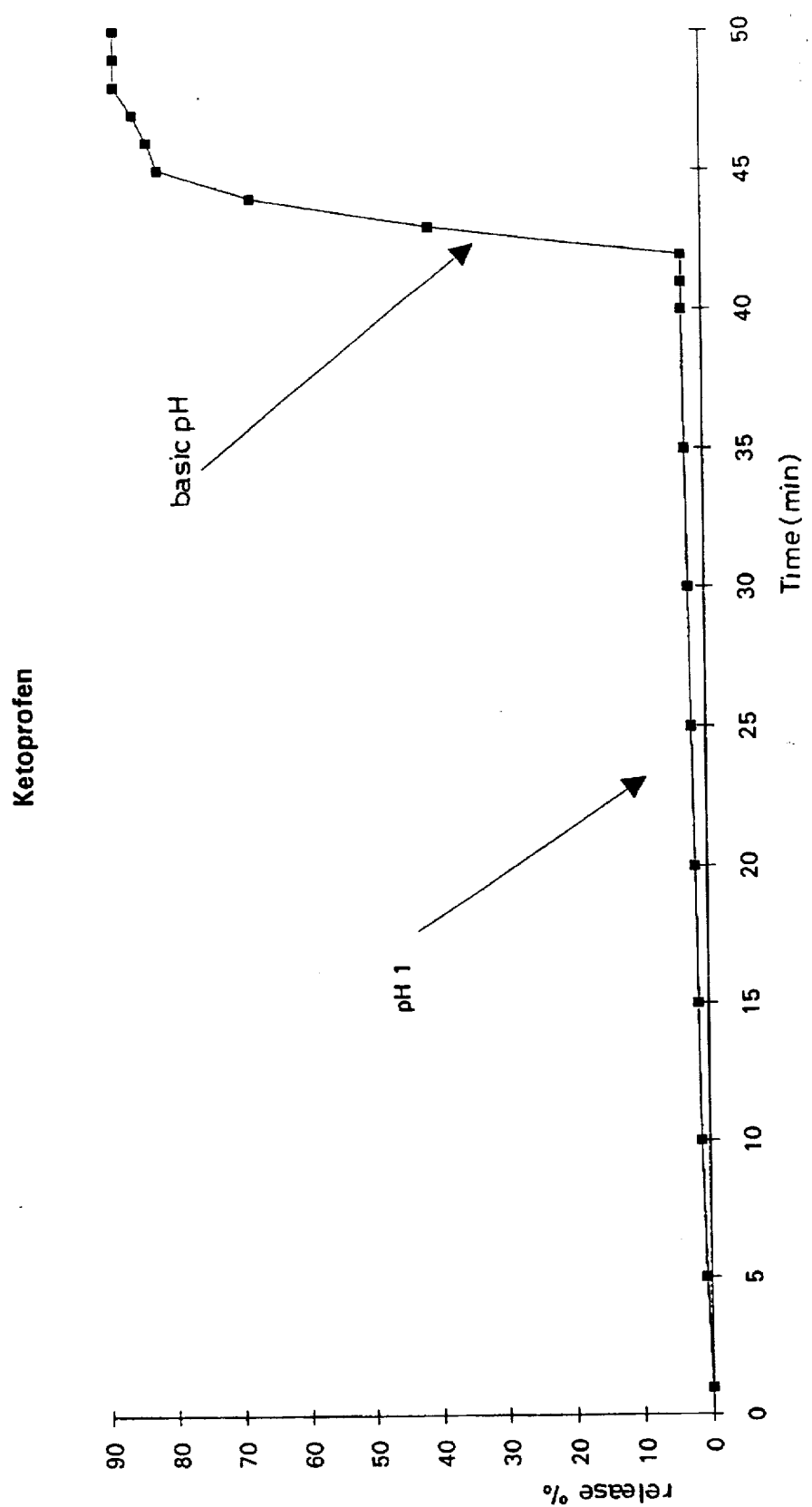
FIG. 3 shows the ketoprofen release at the same conditions.

Example 1 was repeated, but ibuprofen was used as active ingredient instead of ketoprofen. The results of the release rate are reported in FIG. 2.

EXAMPLE 4

Figure 7:
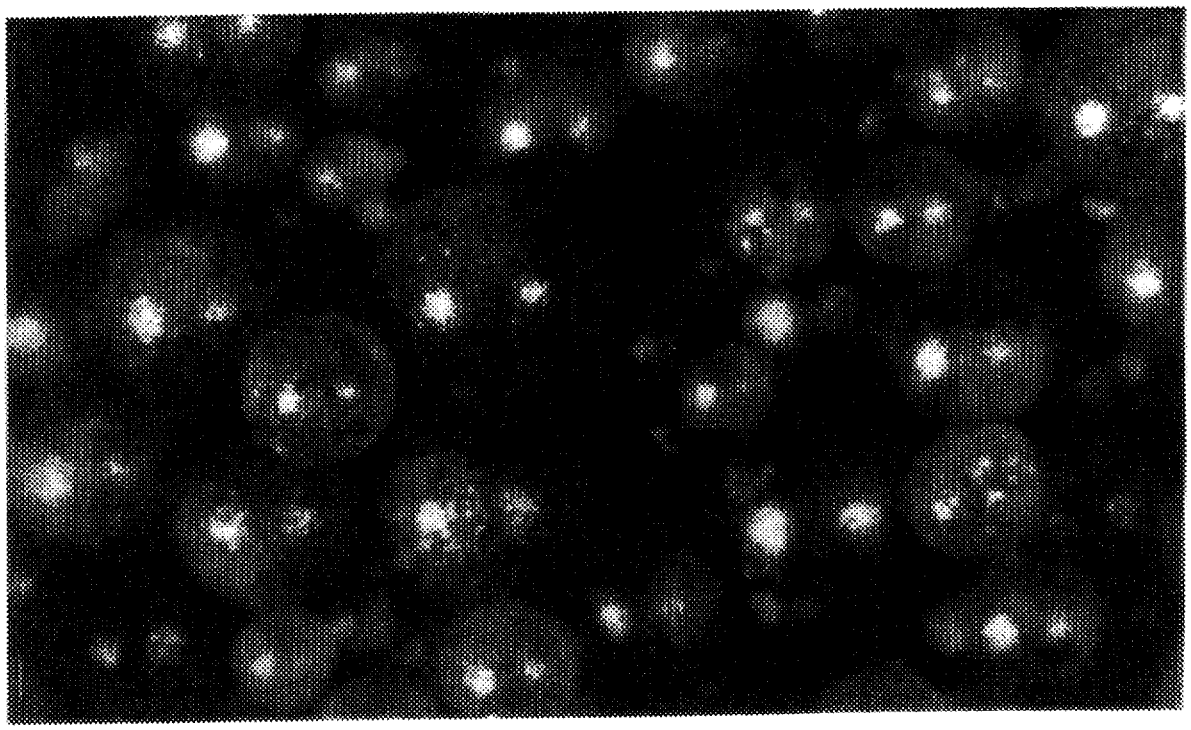
Figure 8:
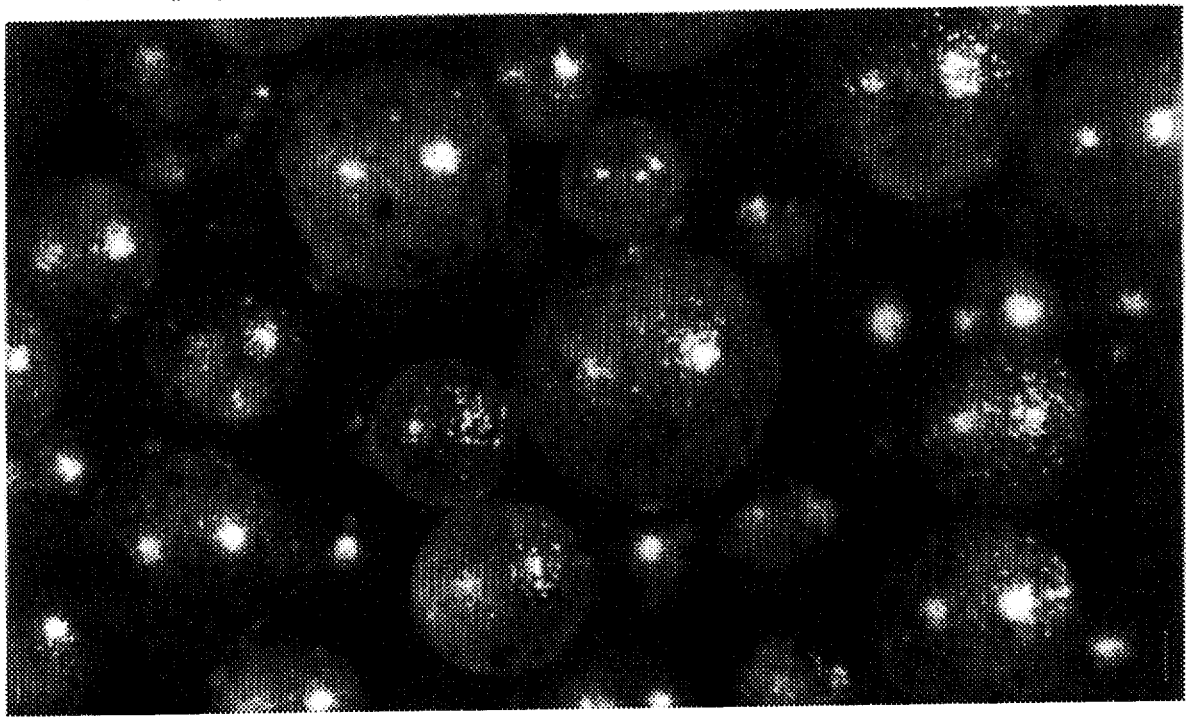

Following the procedure of Example 1, microspheres were obtained containing hydrogenated castor oil (Cutina HR, Trade mark) 45%, karite butter 30%, ferric oxide pigment 25%. A photograph of said spheres (magnitude 100×; here and in the following, the magnification of microphotos is intended as referred to the 24×36 mm slide) is given in FIGS. 7 and 8. The product can be used as an ingredient for cosmetic compositions.

EXAMPLE 5

Figure 9:
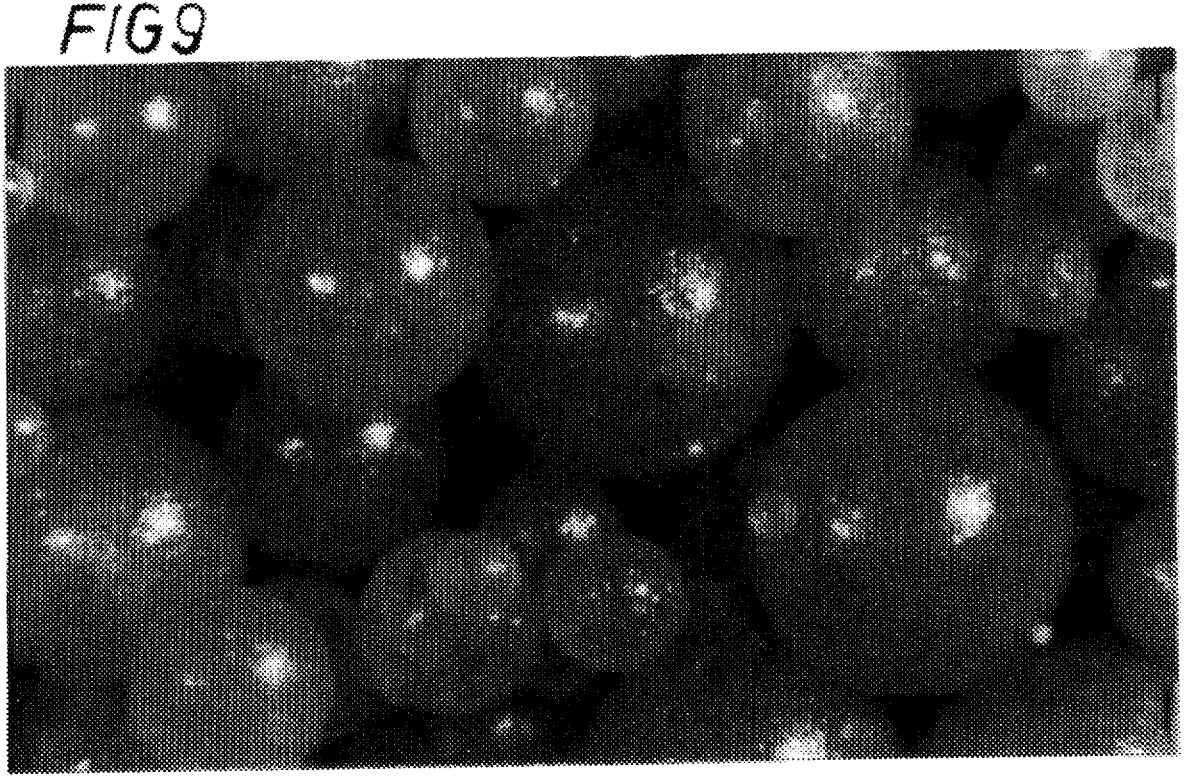
Figure 10:
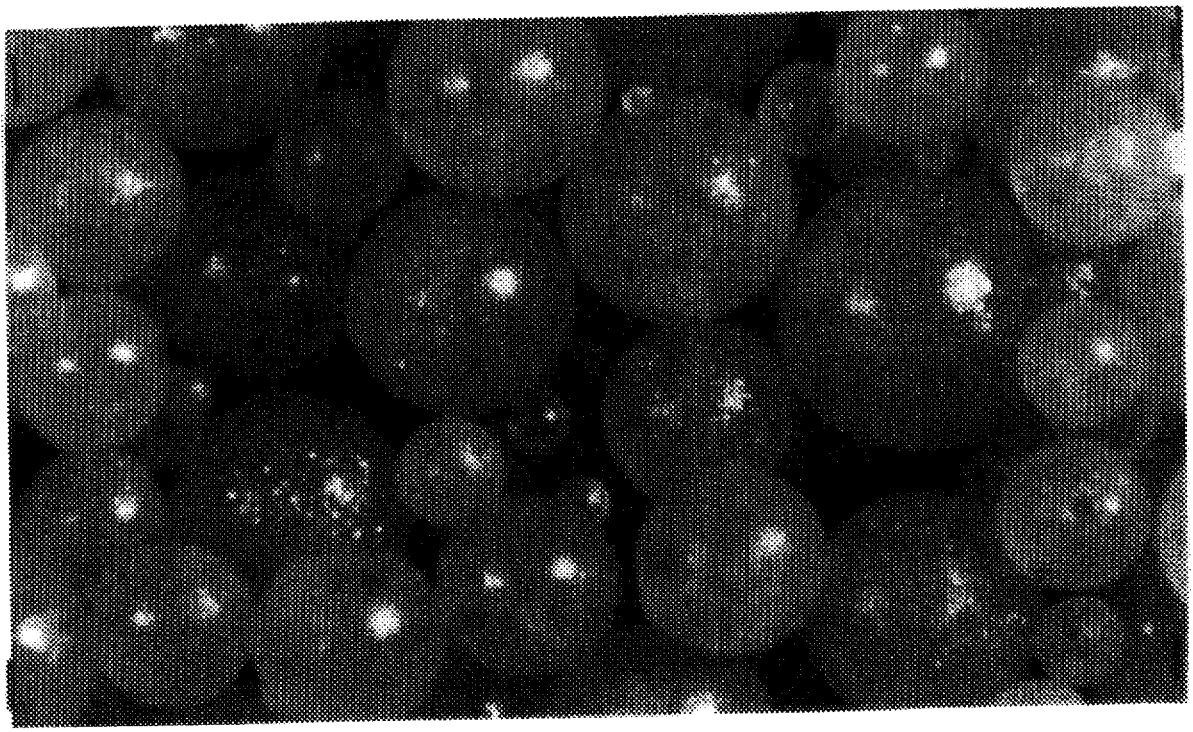

Following the procedure of Example 1, microspheres were obtained containing hydrogenated castor oil (Cutina HR) 45%, karite butter 30%, β-carotene 25%. Photographs (magnitude 100×) in FIGS. 9 and 10. Use as in Example 4.

EXAMPLE 6

Figure 11:
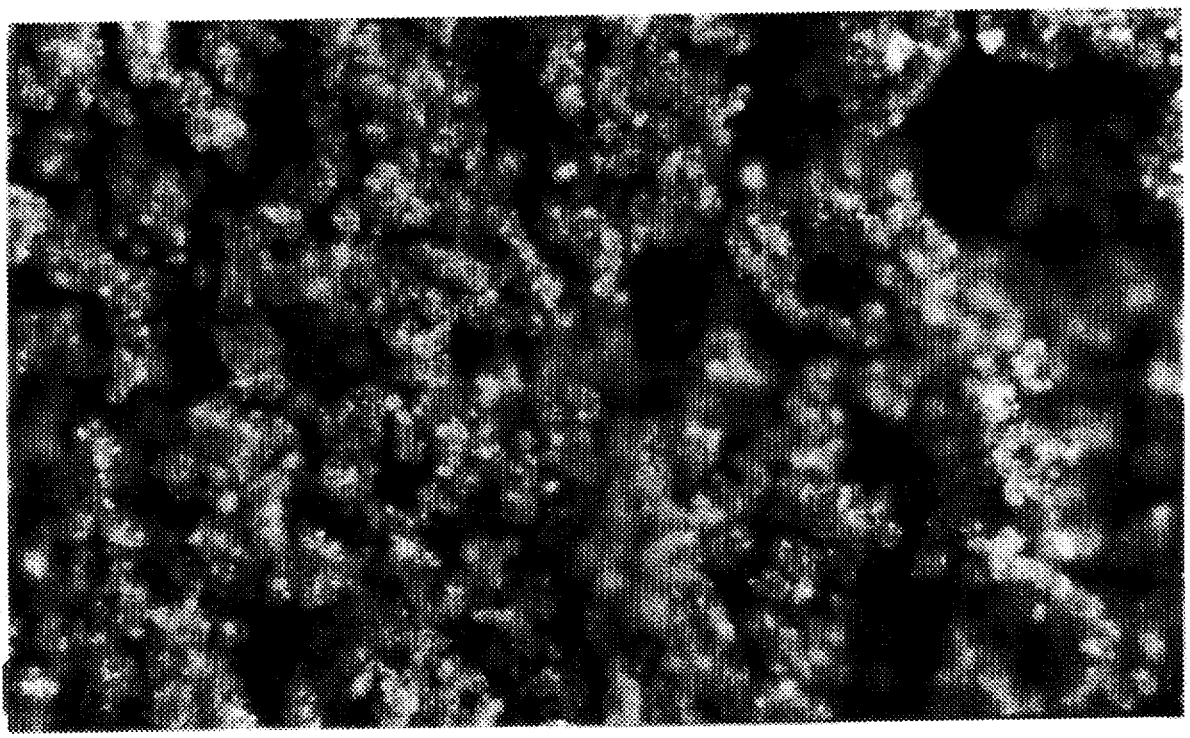
Figure 12:
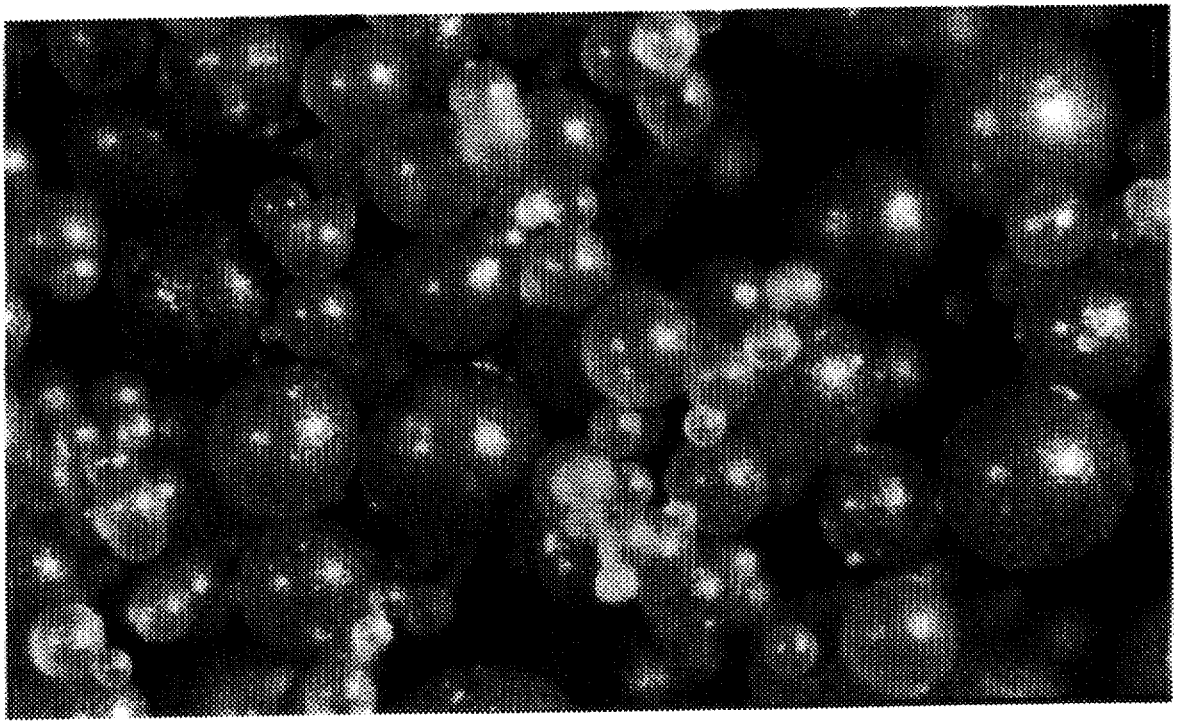
Figure 13:
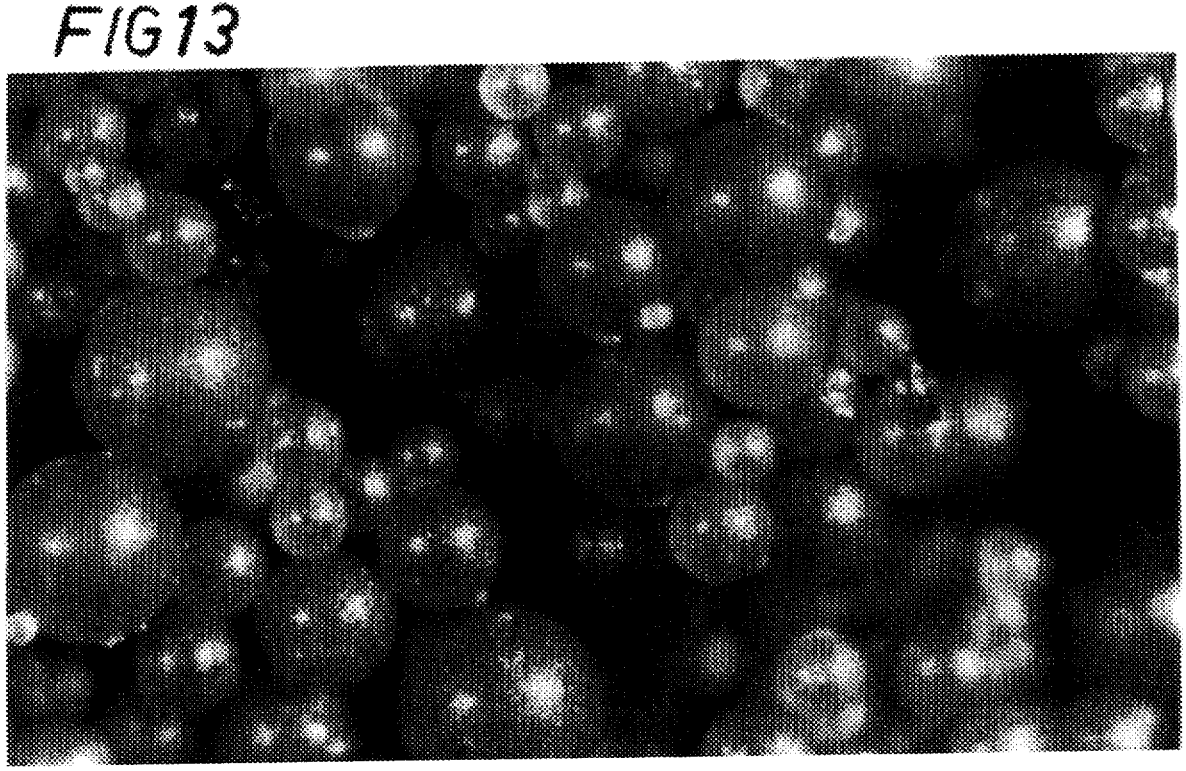
Figure 14:
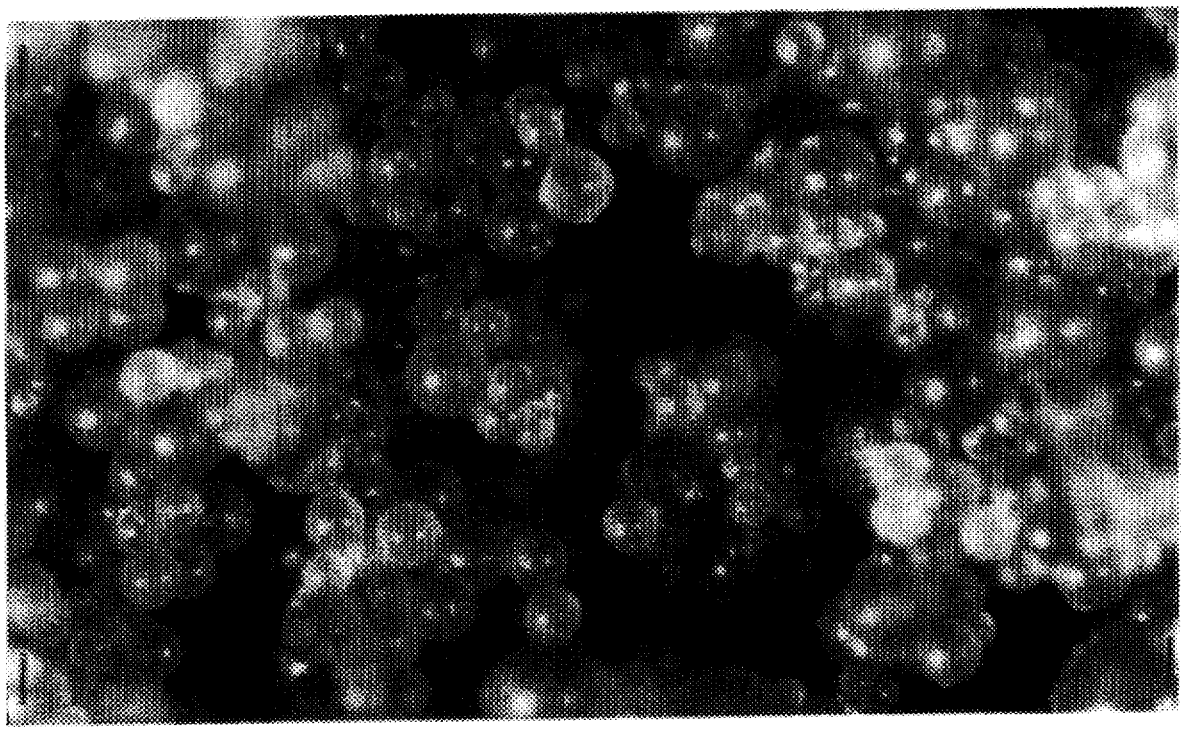
Figure 15:
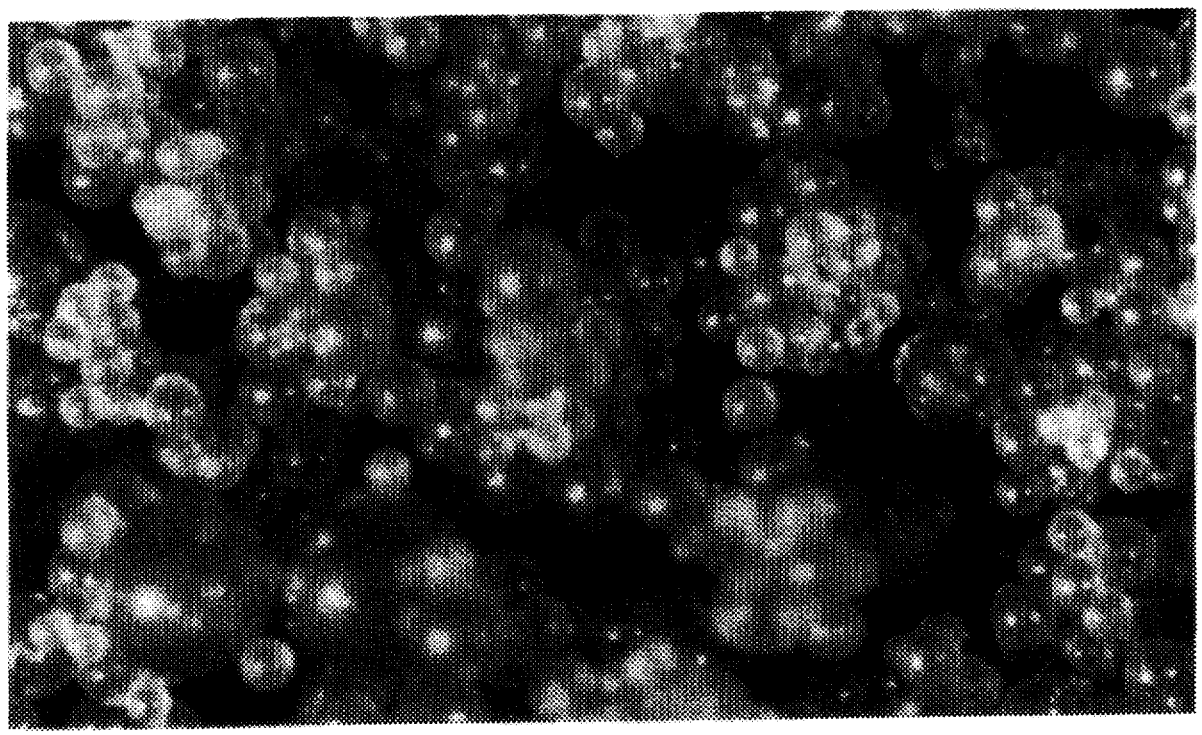

FIG. 11 is a microphotograph (65×) of soluble cacao now on the market, whereas a microphotographs (65×) of soluble cacao powder prepared according to the present invention following spray congealing technique are shown in FIGS. 12 and 13. Said powder comprises: hydrogenated castor oil (Cutina HR) 27.5%, water-disperdible soja lecithin 12.5%, saccharose 5%, lean cacao powder 50%. In FIGS. 14 and 15 a further microphotograph of soluble cacao is shown, comprising: hydrogenated castor oil (Cutina HR) 22.5%, soja lecithin 22.5%, saccharose 5%, lean cacao powder 50%. The technique used was spray congealing: atomization with ultrasounds.

EXAMPLE 7

Figure 16:
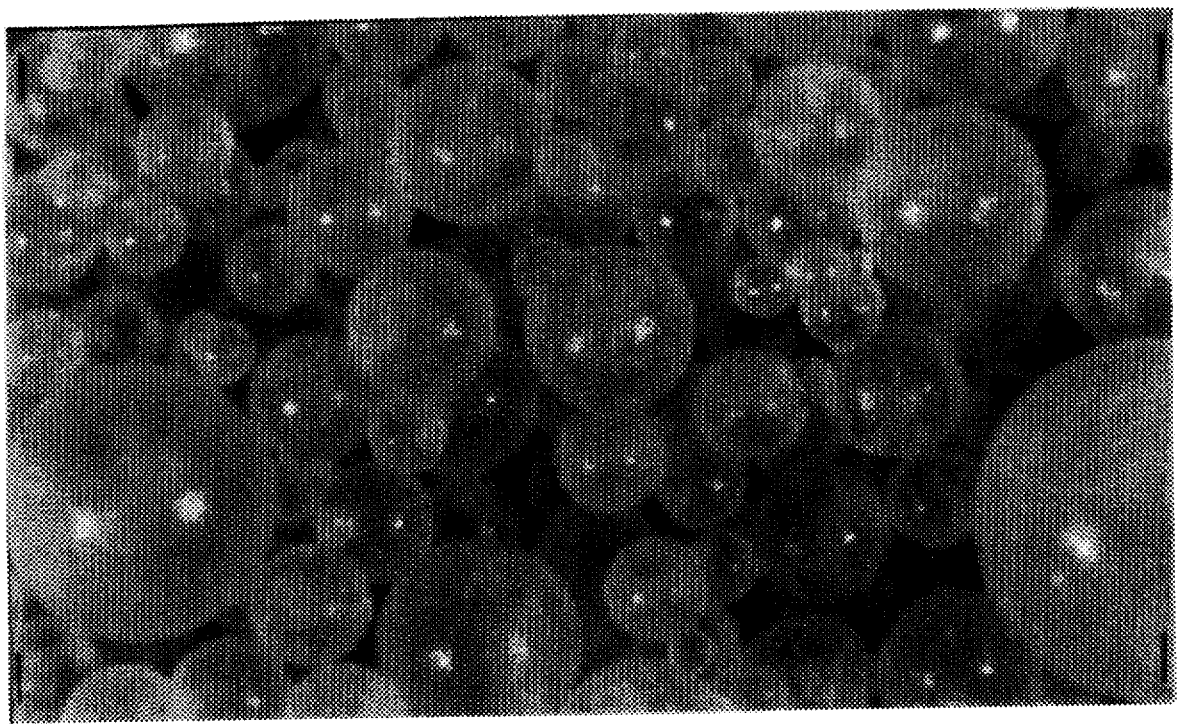
Figure 17:
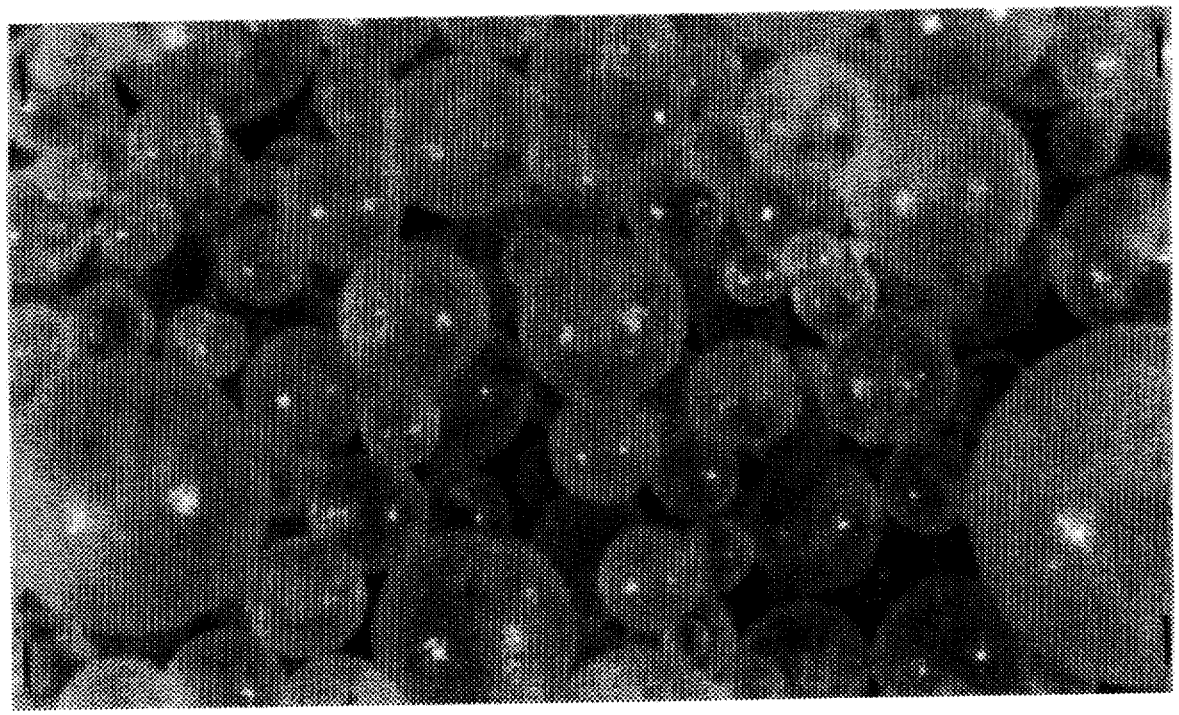

Following the spray congealing procedure and atomization with ultrasounds according to the present invention, microspheres were obtained containing: BRIJ 72 (Trade mark) 24%, hydrogenated castor oil (Cutina HR) 56%, carbaryl malathion 20%. The product is shown in FIGS. 16 and 17. Use as agricultural parasiticide.

EXAMPLE 8

Figure 18:
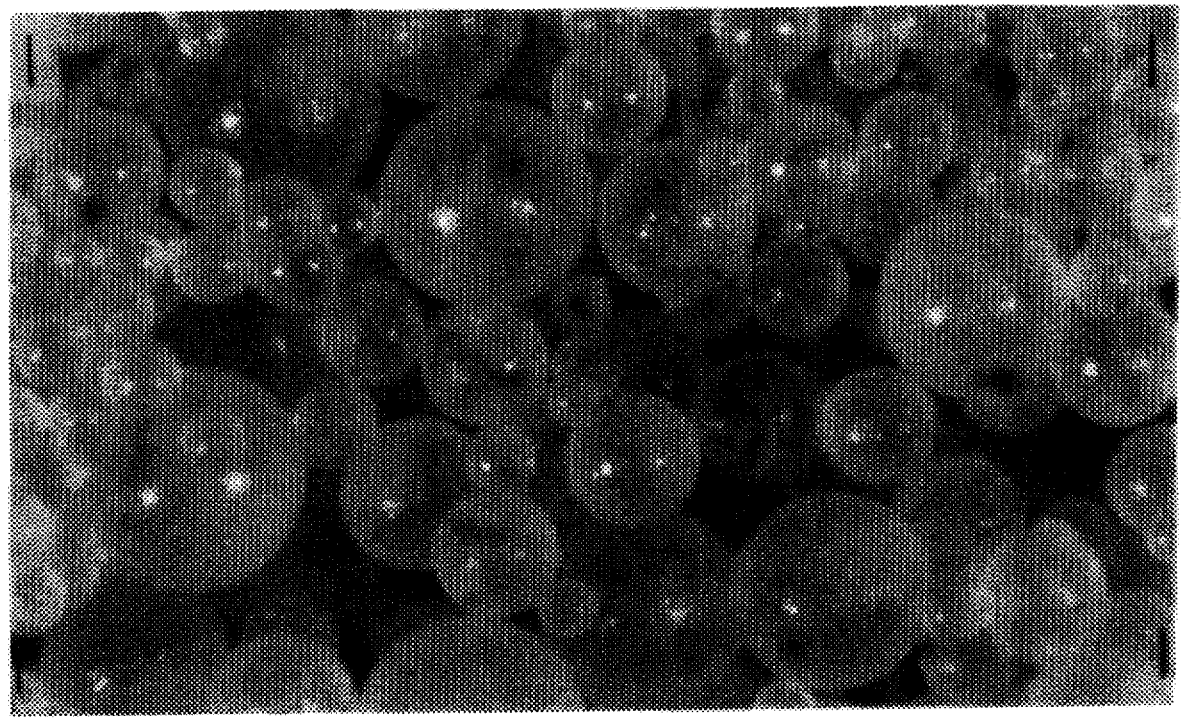
Figure 19:
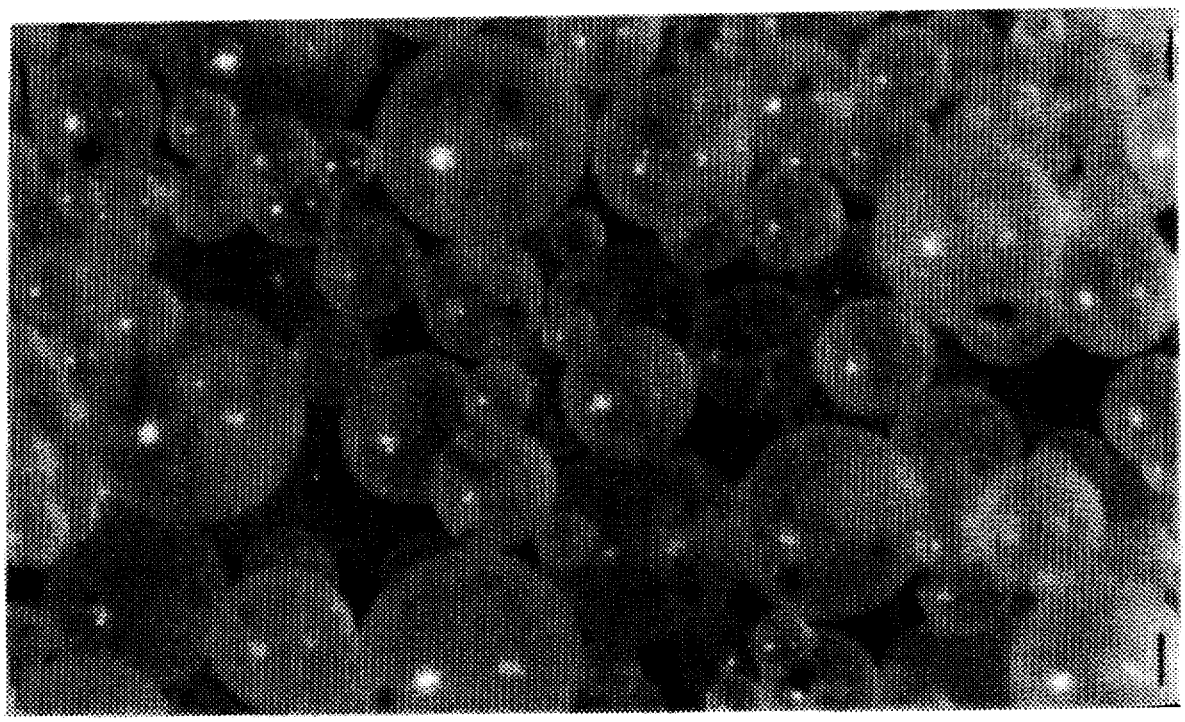

In FIGS. 18 and 19 microspheres are shown (65 X) containing BRIJ 72 16%, hydrogenated castor oil (Cutina HR) 64%, carbaryl malathion 29%.

EXAMPLE 9

Figure 20:
Figure 21:
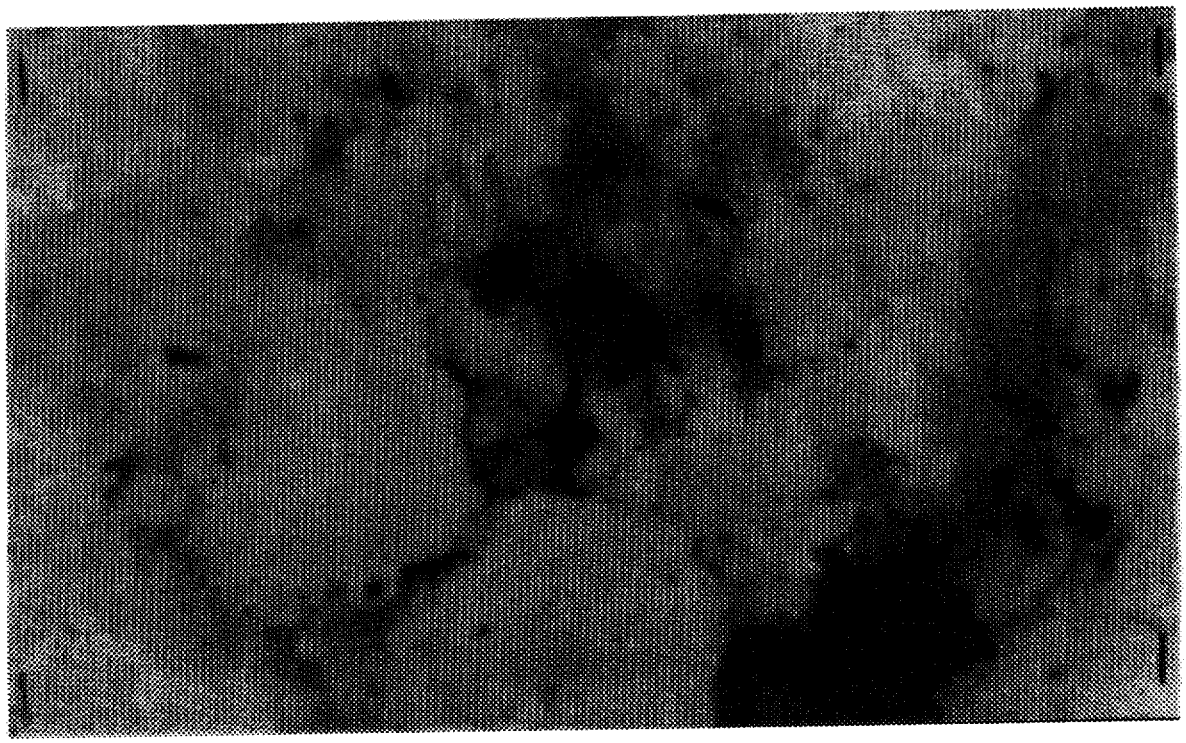

In FIGS. 20 and 21 photographs of whole powder milk are shown (65×), obtained with spray drying technique and ultrasonic atomization.

EXAMPLE 10

Figure 22:
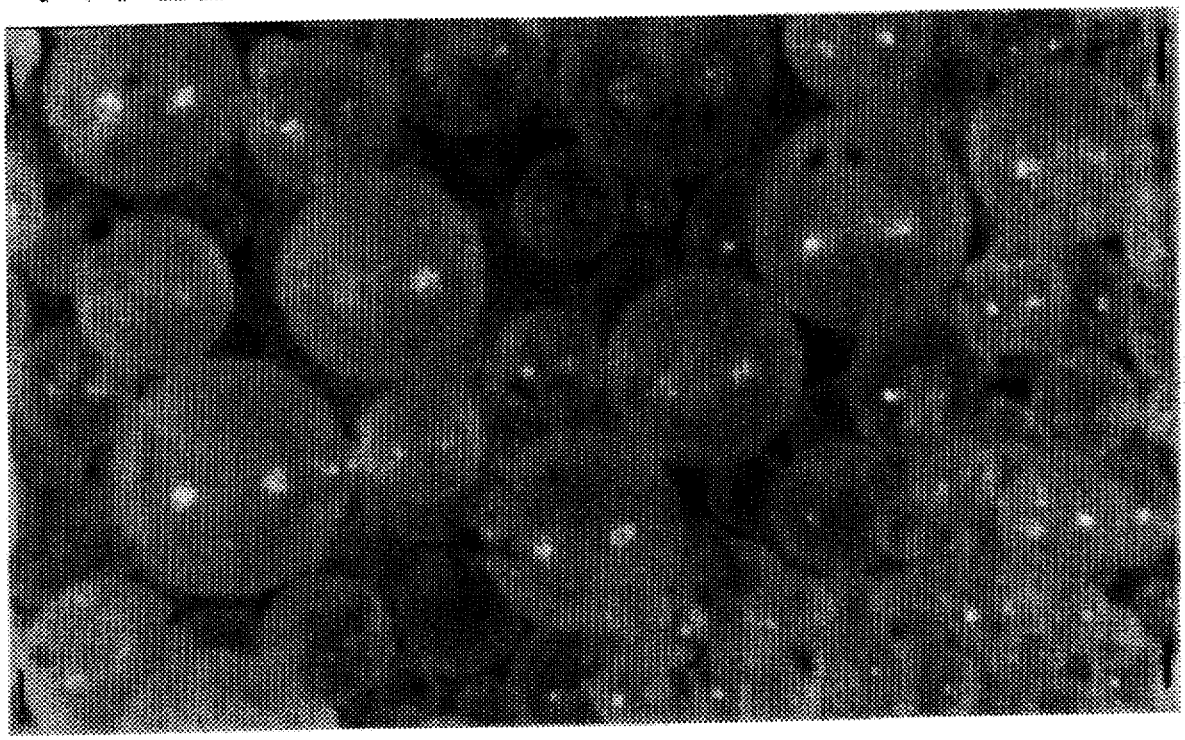
Figure 23:
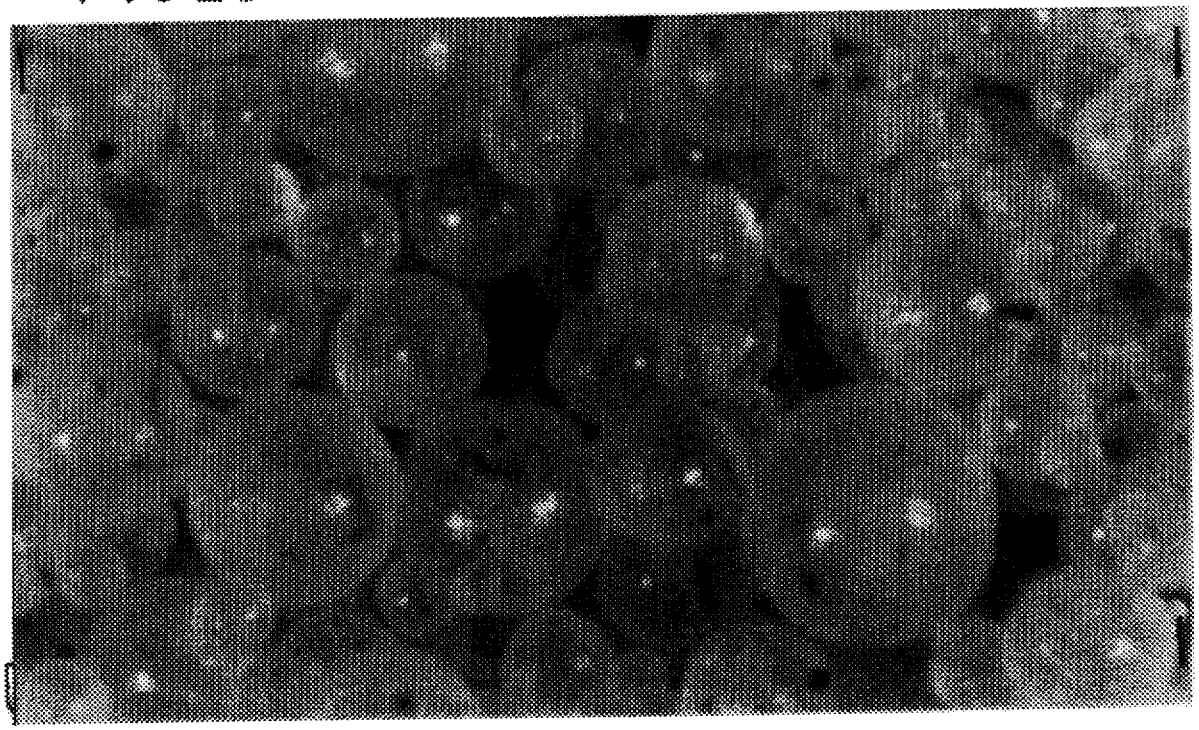

Photographs of microspheres (65×) containing hydrogenated castor oil (Cutina HR) 50%, stearin 15%, swine lard 20%, 3-alpha-acetonyl-benzyl-4-hydroxy-cumarine 15%, are shown in FIGS. 22 and 23. Preparation with spray congealing technique, ultrasonic atomization. Use as rat poison.

We claim:

1. Apparatus for preparing solid forms with controlled release of the active ingredient according to the spray drying and spray congealing techniques, characterized in that is comprises:

a) an atomizing device utilizing mechanical vibrations of resonant metal elements or nozzles, that nebulizes in very little droplets a liquid comprising a solution, suspension or emulsion of one or more active ingredients and/or excipients in one or more solvents of different polarity or of one or more active ingredients in one or more melted waxy excipients;

b) a cylindrical chamber with vertical axis inside of which the droplets thus obtained in a) fall to give spherical powder particles because of the evaporation of the contained solvents or of the solidification owing to the quenching of the melted waxy components, and c) a device for recovering the volatile solvents eventually employed.

2. Apparatus according to claim 1, characterized in that the resonant metal elements comprise appropriately shaped sonotrodes or with application of vibrating elements, for example thin plates, or provided with a nozzle the diameter of which depends on the liquid to be treated.

3. Apparatus according to claim 1, characterized in that the diameter of the droplets obtained in a) is of from 5 to 500 microns.

4. Apparatus according to claim 1, characterized in that the length of the atomized fluid jet is usually of from 25 to 30 cm with a loading of 50 l/h.

5. Apparatus according to claim 1, characterized in that the atomization chamber heigth b) is usually lower than 2 m and the diameter is of 1 m.

6. Apparatus according to claim 1, characterized in that the mechanical frequencies are of from 20 kHz to 150 kHz.

7. Method for preparing solid forms with controlled release of the active ingredient, characterized in that a suspension, solution or emulsion of one or more active ingredients and/or excipients in one or more solvents of different polarity or of one or more active ingredients in one or more melted waxy excipients is fed on resonant metal elements or nozzles subjected to infrasonic, sonic or ultrasonic frequencies, the very small droplets thus obtained fall in a cylindrical chamber with vertical axis to give spherical powder particles, and the solvents eventually employed are recovered.

8. Method according to claim 7, characterized in that the solution, suspension or emulsion fed to the resonant metal elements is an aqueous composition.

9. Method according to claim 7, characterized in that the solution, suspension or emulsion is fed to the resonant metal elements or nozzles in an amount of at least 50 l/h.

10. Method according to claim 7 or 8, characterized in that as resonant metal elements appropriately shaped sonotrodes or with application of vibrating elements, for example thin plate, or provided with a nozzle are employed.

* * * * *